US00PP11296P

United States Patent [19]

Fear et al.

[11] Patent Number: Plant 11,296

[45] Date of Patent: Mar. 21, 2000

[54] PEACH TREE NAMED 'SUPECHEIGHT'

[75] Inventors: Carlos D. Fear, Aptos; Bruce D. Mowrey, La Selva Beach; David W. Cain, Bakersfield, all of Calif.

[73] Assignee: Sun World International, Inc., Bakersfield, Calif.

[21] Appl. No.: 09/007,508

[22] Filed: Jan. 15, 1998

[51] Int. Cl.[7] ..... A01H 5/00

[52] U.S. Cl. ..... Plt./197

[58] Field of Search ..... Plt./198, 197

[56] References Cited

U.S. PATENT DOCUMENTS

P.P. 4,903 10/1982 Weinberger ..... Plt./198
P.P. 5,503 7/1985 Weinberger ..... Plt./198

*Primary Examiner*—Howard J. Locker
*Assistant Examiner*—Wendy A Baker
*Attorney, Agent, or Firm*—Knobbe, Martens, Olson & Bear, LLP

[57] ABSTRACT

A new and distinct variety of peach tree characterized by its early ripening fruit which has a round shape, a medium size, and 90–100%% red blush.

1 Drawing Sheet

BACKGROUND AND SUMMARY OF THE INVENTION

This invention relates to the discovery and asexual propagation of a new variety of hybrid peach tree, *Prunus persica* cv. Supecheight. The tree produces a medium-sized and round shaped fruit that has 90–100% red blush, characteristics which make the variety commercially desirable for market use. The new peach tree variety arose in a controlled cross made and first selected by Carlos D. Fear and was found to be stable through subsequent generations of asexual propagations, made in the vicinity of Wasco, Kern County, Calif. Supecheight was evaluated by Bruce D. Mowrey and David W. Cain and was asexually propagated by Carlos D. Fear. Its pollen parent is Supechthree (U.S. Plant Pat. No. 4,903) and its seed parent is Supechfour (U.S. Plant Pat. No. 5,503).

The new peach tree variety cv. Supecheight may be distinguished from other presently available peach cultivars, particularly the Maycrest cultivar (U.S. Plant Pat. No. 4,064), by the following combination of characteristics: a higher percent of red blush (Supecheight has 90–100% red blush as compared to Maycrest's 70–80%), a more smooth and desirable round shape, a lower frequency of undesirable double fruits, a lower chilling requirement (Supecheight requires 550 hours below 45° F. compared to Maycrest's 650 hours), blooming that occurs about 10 days earlier than Maycrest, and ripening that occurs 5 days after the Maycrest variety.

Likewise, the Supecheight variety may be distinguished from the P.F. 5B Variety (U.S. Plant Pat. No. 9,850), by ripening approximately one week earlier, by having showy flower type (Sh/-) as opposed to the nonshow type (sh/sh), by having a melting (M/-) as opposed to a nonmelting (m/m) flesh type, and by having a smoother, less striped or mottled red coloration pattern. The new variety holds these distinguishing characteristics through succeeding asexual propagations, as for example, by budding.

The characteristics which distinguish the new variety of peach tree from its pollen parent, Supechthree, are its higher percent of red blush (Supecheight has 90–100% red blush as compared to Supechthree's 70–80% ) and its ripening approximately 5 days after Supechtree. Supecheight also produces larger and more firm fruit than its pollen parent.

The new variety may be distinguished from its seed parent, Superchfour, in that the new variety ripens approximately 10–14 days earlier, and has a slightly smaller fruit size.

BRIEF DESCRIPTION OF THE FIGURE

FIG. 1 also illustrates an iolated stone viewed in profile. The colors illustrated are as accurate as reasonably possible to attain in color photographic reproductions of this type.

DETAILED BOTANICAL DESCRIPTION OF THE INVENTION

Figure 1:
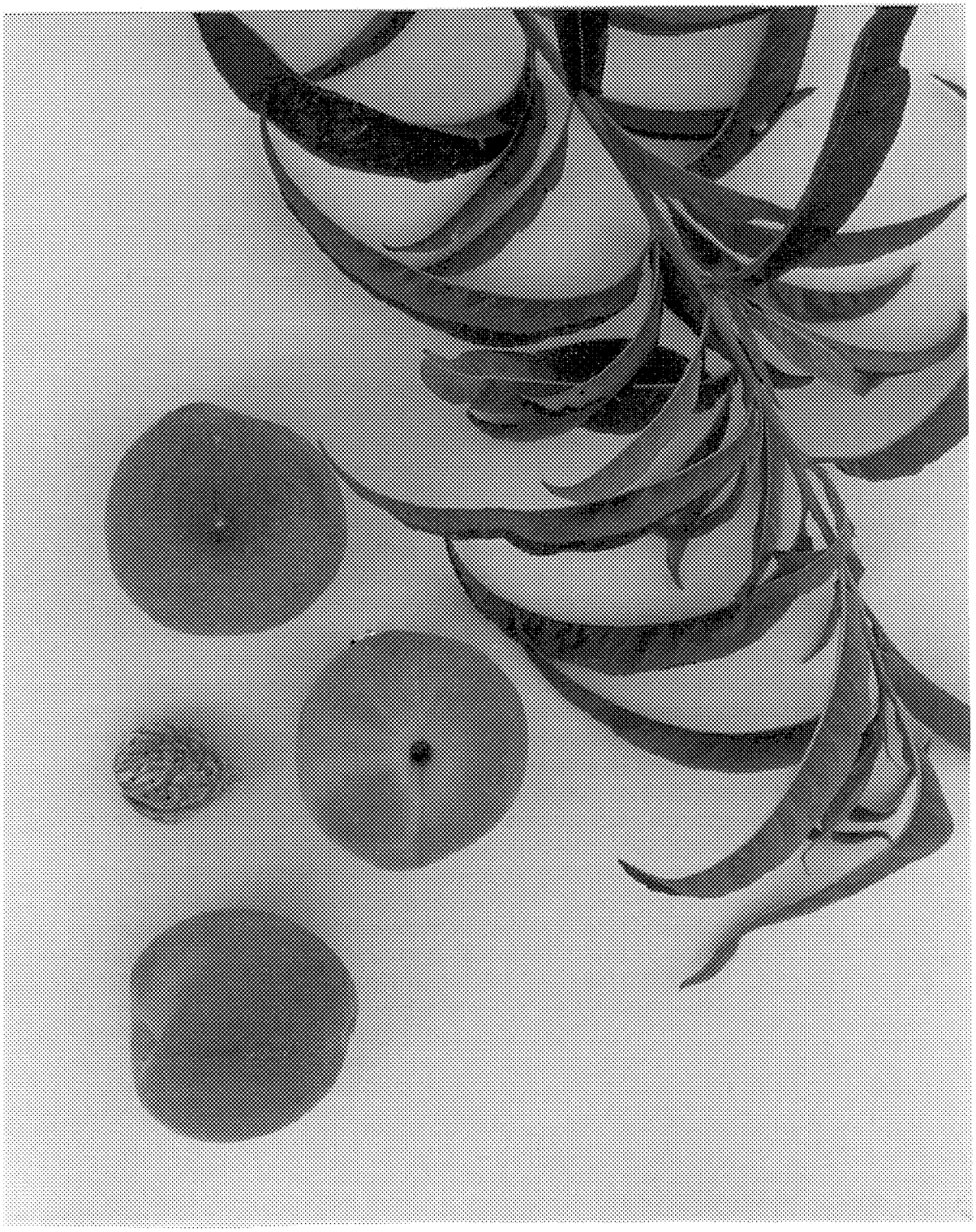
FIG. 1 illustrates, in full color, a typical stem and mature leaves of the peach tree and the ripe fruit as viewed from the stem and in profile.

Throughout this specification, color names beginning with a small letter signify that the name of that color, as used in common speech, is aptly descriptive. Color names with capital letters designate values based upon The R.H.S. Colour Chart, published by The Royal Horticultural Society, London. The botanical description herein follows the UPOV test guidelines for peach varieties.

The descriptive matter which follows pertains to peach trees of the new variety grafted onto Nemared root stock and grown in the vicnity of Wasco, Kern County, Calif. during 1994 and is believed to apply to plants grown under similar conditions of soil and climate elsewhere. Such trees were four years old, and were maintained at height of about 10 feet and a crown diameter of about 10 feet by annual prunings.

TREE

When grafted on Nemared root stock the tree is of medium size and vigor, typical of standard commercial peach varieties grown in California. Trees of the variety typically produce about 78 cm.-long lateral shoots (total length) when grown under normal commercial culture. Trees are upright in habit and vase formed in shape. The foliage is of medium density. The trees are hardy, productive, and are regular bearers, producing about 19.2 bins per acre (approximately 16.160 pounds per acre).

The trunk is of medium shape and its surface texture is medium, exhibiting slight exfoliation of the bark . The trunk coloration is R.H.S. 201 D (gray) at a height of 30 cm. above the ground, and R.H.S. 200 D (brown) at a height of 60 cm. above the ground. The circumference of the trunk is approximately 47.6 cm. at a height of 30 cm. above the ground for a four year-old tree. The branches are medium to slender in shape and have a surface texture that is medium, as well. The branches are smooth, semi-glossy in surface appearance, and are Grey-Brown 199B in color. The number of lenticels on the trunk and main branches is medium, approximately 3 per square centimeter. Lenticels average 6.9 mm. long and 1.5 mm. wide.

LEAVES

In general, leaves are of a medium size, having an average length of about 16.1 cm. and an average width of about 4.5 cm. Leaves are lanceolate in outline and upfolded in profile. Leave blade tips curve downwardly at an acute angle. The leaf margin is crenate, and undulation of the margin is slight. The leaf is cuspidate at the apex, V-shaped at the base, and of medium thickness. The upper surface of the leaf is about Yellow-Green 147B in color, and of weak glossiness. The upper leaf surface is smooth with a dull appearance; pubescence is absent. The lower leaf surface is about Yellow-Green 147B in color, and weak in glossiness. Pubescence is absent from the lower surface which has a smooth texture and a dull appearance.

The petiole is medium to short in length and has a medium thickness. There is an average of 3.2 small, globose glands (Yellow-Green 153C in color) alternately positioned on both the leaf base and the petiole. Stipules fall off.

Wood (leaf) buds are small to medium in size and ovoid in shape. Their position, relative to the shoot, is adpressed. Their support is small and not decurrent. The time of bud burst is medium.

On flowering shoots anthrocyanin coloration is present in medium intensity. The shoots are of thin to medium thickness, about 0.4 cm., and internode length is also medium, about 2.8 cm. The density of buds is medium and they are generally isolated on one-year-old shoots. The ratio of wood (leaf) buds to flowering buds is about 9:22.

FLOWERS

Flower buds are hardy, of medium size and length, plump, and adpressed. Flower buds are pubescent and about Greyed-Orange 165A in color.

Flowers first bloom by about Feburary 24 and attain full bloom by about March 2 in Wasco, Kern County, Calif.—a time of bloom that is early to medium as compared with similar varieties in the growing area. Blooms have a medium duration, and a medium to large size (diameter of the fully opened flower is about 4.4 cm.). The shape of the bloom is rosaceous and its petals are free. The fully opened flower is about Red-Purple 62D in color.

The peduncle is medium in length and thickness, and pubescence is absent. The receptacle is of medium depth. Pubescence of the inner surface (at white bud stage) is sparse and pubescence of the outer surface is absent.

Sepals are adpressed to petals, ovate in shape, and have no pubescence on the inner surface. The outer surface, in contrast, is pubescent. None of the flowers have exhibited double sepals.

Petals are medium to large in size, about 1.5 cm. wide, obovate in shape, have short to medium claw length, strong to medium margin waviness, and a wide base angle. The division of the upper margins is entire, and pubescence is absent on both inner and outer surfaces. The inner and outer surfaces are about Red-Purple 62D in color. No flowers having double petals have been observed.

The stigma is positioned slightly above the anthers. The anthers are about Red-Purple 61B in color just before dehiscence. Pollen is about Yellow 13A in color. Stamens are perigynously positioned. The number of pistils is sometimes more than one but the frequency of supplementary pistils is few. The ovary and style are pubescent and both display a medium density of hairs.

FRUIT

The fruit, as described, was firm to ripe at maturity on May 15, 1993. The fruit at firm ripe maturity is medium in size and has an axial diameter of 5.7 cm. and a transverse diameter in the suture plane of 5.7 cm. At right angles to the suture plane, the diameter is about 6.0 cm., thus indicating a slight unsymmetrical to globose shape. The average fruit weight is about 90 grams. The position of the maximum diameter is towards the middle of the fruit. The fruit is asymmetric about the suture line. The fruit ripens very early; commercial harvest typically begins about May 16, and the last pick date is about May 24 in a normal year.

The fruit is for market use and has a good keeping quality and good shipping quality. The fruit exhibits no unusual susceptibility to insects and diseases when grown under normal conditions.

The suture extends from the base to the apex and the ventral surface is rounded with equal lips. Depression of the apex is indistinct and pubescence at the apex is medium with an average to high density. The pistil base is persisting.

The stem cavity is flaring and elongated in the suture plane with the suture showing on both sides. The depth of the cavity is about 0.7 cm., its breadth is about 2.5 cm. and there are no markings. The base of the fruit is rounded. The apex is mammiform in shape and the pistil point is apical in shape.

The stem is about 0.7 cm. in length and a medium structure. Adherence to the stone is weak. The skin is a medium thickness and texture and is not tenacious to the flesh. The skin is without roughness or reticulation and shows no tendency to crack in dry seasons. Ground color of the skin is about Yellow 13B and the over color of the skin is about Red-Purple 60B. Down is abundant, medium to short, rolls up when rubbed, and bloom is absent.

The color of the flesh, including at the surface of the pit cavity, is about Yellow-Orange 14C. Amygdalin in wanting and juice is abundant to moderate. The flesh has a medium sugar content. The flesh texture is medium and melting, with tender-fibers. Fruit ripens unevenly (earliest at the apex), has a distinct aroma, and is of good eating quality. The stone (endocarp) is approximately 0.7 grams and the flavor is delicate.

The stone is semi-free and adheres to flesh along dorsal and ventral edges. Fibers are long and fiber-like threads along the ridges are retained. The stone is medium to small in size, being about 3.4 cm. in length, 2.6 cm. in breadth, 1.8 cm. thick, and has a stalk end width of about 0.7 cm. The angle of the stalk end is obtuse. The form of the stone in profile is oval and cuneate toward the apex. The form in ventral view is sub-globular. The stone's base is nearly straight, its apex is acuminate, and its hilum is oblong in shape. The position of the stone's maximum breadth is towards the pistil end and the sides are slightly unequal. The surface of the stone is irregularly furrowed near the base and is pitted throughout. An outgrowing keel is absent. The ridges are jagged towards the base and the pits are angular. The ventral edge of the stone is medium to thick and the dorsal edge has a continuous broad groove throughout. The color of the stone is about Greyed-Yellow 162C. The stone has a slight tendency to split in a dry season.

What is claimed is:

1. A new variety of peach tree cv. Supecheight, as illustrated and described herein.

* * * * *